United States Patent [19]
Nagano et al.

[11] Patent Number: 5,225,862
[45] Date of Patent: Jul. 6, 1993

[54] VISUAL AXIS DETECTOR USING PLURAL REFLECTED IMAGE OF A LIGHT SOURCE

[75] Inventors: Akihiko Nagano, Kawasaki; Kazuki Konishi, Hino; Tokuichi Tsunekawa, Yokohama, all of Japan

[73] Assignee: Canon Kabushiki Kaisha, Tokyo, Japan

[21] Appl. No.: 807,621

[22] Filed: Dec. 13, 1991

Related U.S. Application Data

[63] Continuation of Ser. No. 662,327, Feb. 25, 1991, which is a continuation of Ser. No. 475,756, Feb. 6, 1990.

[30] Foreign Application Priority Data

Feb. 8, 1989 [JP] Japan .................................. 1-28967

[51] Int. Cl.$^5$ .............................................. G03B 13/02
[52] U.S. Cl. ..................................... 354/62; 354/400; 354/195.1; 354/219; 354/410
[58] Field of Search ................... 354/62, 195.1, 195.11, 354/195.12, 195.13, 405, 404, 219, 410

[56] References Cited

U.S. PATENT DOCUMENTS

| | | | |
|---|---|---|---|
| 2,724,305 | 11/1955 | Brandt | 354/62 |
| 3,543,666 | 12/1970 | Kazel | 354/405 |
| 3,936,849 | 2/1975 | Tsujimoto | 354/195.1 |
| 4,287,410 | 9/1981 | Crane et al. | 250/201 |
| 4,574,314 | 3/1986 | Weinblatt | 354/195.1 |
| 4,828,381 | 5/1989 | Shindo | 354/62 |
| 4,836,670 | 6/1989 | Hutchinson | 354/62 |
| 4,950,069 | 8/1990 | Hutchinson | 354/62 |
| 5,036,347 | 7/1991 | Tsunekawa et al. | 354/62 |

FOREIGN PATENT DOCUMENTS 61-172552 8/1986 Japan .

OTHER PUBLICATIONS

Magazine article entitled "Accurate two-dimensional eye tracker using first and fourth Purkinje images", vol. 63 (Aug. 1973), No. 8, pp. 921-928.

*Primary Examiner*—Russell E. Adams
*Attorney, Agent, or Firm*—Fitzpatrick, Cella, Harper & Scinto

[57] ABSTRACT

An optical apparatus which detects a visual axis using plural reflected images of a light source includes an observation device with which an observer observes an object. An image sensor is provided for generating a signal and response to an image. Optical structure is provided for forming a plurality of reflected light source images on the image sensor by reflection of light from the eye of the observer. The optical structure includes (1) an illumination assembly for projecting a light beam from at least one light source to the eye of the observer, and (2) a convergence component having at least one convergent lens for converging the light beam reflected from the eye of the observer, to produce the plurality of reflected light source images. The optical structure includes at least two light sources and/or two convergent lenses. An electrical circuit is coupled to the image sensor for generating (1) information relating to a working distance between the plurality of reflected light source images reflected from the eye, and (2) information relating to the reflected image of a front eye part, to generate information relating to a direction of the visual axis of the eye.

24 Claims, 5 Drawing Sheets

VISUAL AXIS DETECTOR USING PLURAL REFLECTED IMAGE OF A LIGHT SOURCE

This application is a continuation of application Ser. No. 07/662,327 filed Feb. 25, 1991; which is a continuation of application Ser. No. 07/475,756 filed Feb. 6, 1990.

BACKGROUND OF THE INVENTION

1. Field of the Invention

The present invention relates to a visual axis detector, and more particularly to a visual axis detector which detects a direction of gazing point (visual axis) along which an observer (photographer) observes on an observation plane on which an object image is formed by a lens system of an optical device such as a camera, by utilizing a reflection image which is formed when an eyeball plane of the observer is illuminated.

2. Related Background Art

Various types of visual axis detectors for detecting the viewing direction (visual axis) along which the observer observes on the observation plane have been proposed.

For example, in Japanese Laid-Open Patent Application No. 61-172552, a light beam from a light source is directed to a front eye portion of an eye-ball under test and the sight axis (gazing point) is determined by making use of a focusing state of a reflection image due to a reflected light from a cornea and an iris.

FIG. 6 illustrates the visual axis detection method proposed in the above Patent Application, with a modification for illustration purpose.

In FIG. 6, numeral 104 denotes a light source such as a light emitting diode which emits an infrared ray which is insensitive to the observer. It is arranged on a focus plane of a projection lens 106.

The infrared ray emitted from the light source 104 is collimated by the projection lens 106, reflected by a half-mirror 110 and illuminates a cornea 1 of an eyeball 101. A portion of the infrared ray reflected by the surface of the cornea 1 passes through the half-mirror 110 and is focused by a lens 107 to a position d' on an image sensor 109. Symbol d represents a first Purkinje's image which is a reflected virtual image of the light source by the cornea. Ends a and b of the iris 3 are focused to positions a' and b' on the image sensor 109 through the lens 107. When a rotation angle $\theta$ of an optical axis B of the eyeball relative to an optical axis A of the lens 107 is small, a coordinate $Z_c$ of a center position c of the iris 3 is represented by $$Z_c \approx \frac{Z_a + Z_b}{2}$$

where $Z_a$ and $Z_b$ are coordinates of the ends a and b of the iris 3.

The rotation angle $\theta$ of the optical axis B of the eyeball substantially meets a relationship of $$\overline{OC} \cdot \sin\theta \approx Z_c - Z_d \qquad (1)$$

where $Z_d$ is a Z-coordinate of the position d at which the first Purkinje's image appears, and $\overline{OC}$ is a distance from a center of curvature 0 of the cornea 1 and a center C of the iris 3. Thus, the rotation angle $\theta$ of the optical axis B of the eyeball can be determined by detecting the position of each of the peculiar points (the first Purkinje's image position d and the ends a and b of the iris) projected on the image sensor 109. The formula (1) may be modified to $$\beta \cdot \overline{OC} \cdot \sin\theta \approx \frac{Z_a' + Z_b'}{2} - Z_d' \qquad (2)$$

where $\beta$ is a magnification determined by a distance $l_1$ between the position d of the first Purkinje's image and the lens 107, and a distance $l_0$ between the lens 107 and the image sensor 109. Normally, it may be regarded as a substantially constant value.

By incorporating a device which detects the visual direction (gazing point) of the eye of the observer under test into a finder of a one-eye reflex camera, it is possible to determine which position on a pint glass the photographer is observing.

This is advantageous in an automatic focus detector having distance measurement points not only at the center of field but also at a plurality of points in the field. Namely, when the observer attempts to make the automatic focus detection by selecting one of the distance measurement points, a process to input the selected one point may be omitted but the point which the observer is observing is regarded as the distance measurement point so that the distance measurement point is automatically selected to effect the automatic focus detection.

However, when the visual axis detector proposed in the Japanese Laid-Open Patent Application 61-172552 is applied to detect the visual axis of the observer who observes through the finder of the camera, there is a problem if a working distance between the visual axis detection optical system comprising illumination means and photo-detection means, and the eyeball of the observer is not constant but variable. For example, assuming that the distance $l_1$ between the lens 107 and the position d of the first Purkinje's image in FIG. 6 is not a predetermined value but different from that value, the magnification $\beta$ defined by the formula (2) is not constant. As a result, an error is induced in the calculation of the rotation angle $\theta$ of the optical axis of the eyeball.

As a result, the observer must make a manual calibration so that the gazing point of the observer matches to an index indicated by the visual axis detector. This is very troublesome.

Another method for detecting the visual axis is described in JOSA Vol. 63, No. 8 p.921 et seq, and U.S. Pat. No. 4,574,314 discloses a technique to apply the detection of the eye movement to an auto-focusing system of a television camera.

A related technology is described in U.S. patent application Ser. No. 406,588 assigned to the present assignee.

SUMMARY OF THE INVENTION

It is an object of the present invention to provide a visual axis detector of a simple construction which can always precisely detect an observation point of an observer on an observation plane or a visual axis of the observer, by providing distance detection means for detecting a distance between a predetermined plane of the visual axis detector and a predetermined point of an eyeball of the observer, without needing the calibration of the visual axis by the observer himself.

It is another object of the present invention to project one or more light source to the eyeball of the observer, focus a plurality of reflected light source images from a front eye portion onto an image plane by optical means, determine a distance between the predetermined plane of the illuminating light source or the optical means and the predetermined position of the eyeball of the observer by the distance detection means, and calculate the visual axis of the observer by calculation means by making use of output signals from an iris image, the optical means and the distance detection means.

DESCRIPTION OF THE PREFERRED EMBODIMENTS

Figure 1:
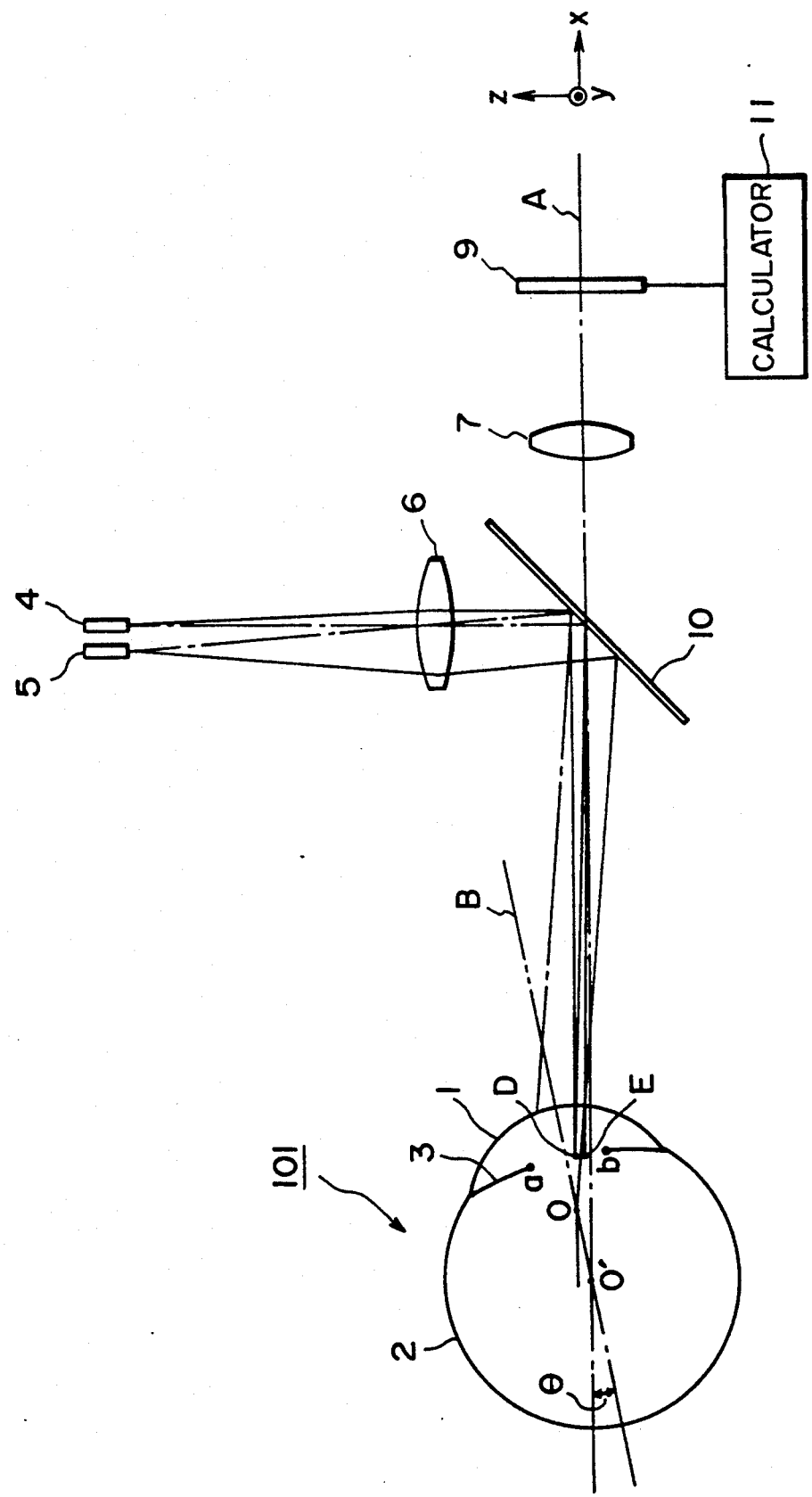
FIG. 1 shows an optical sectional view of a first embodiment of the present invention.
Figure 2A:
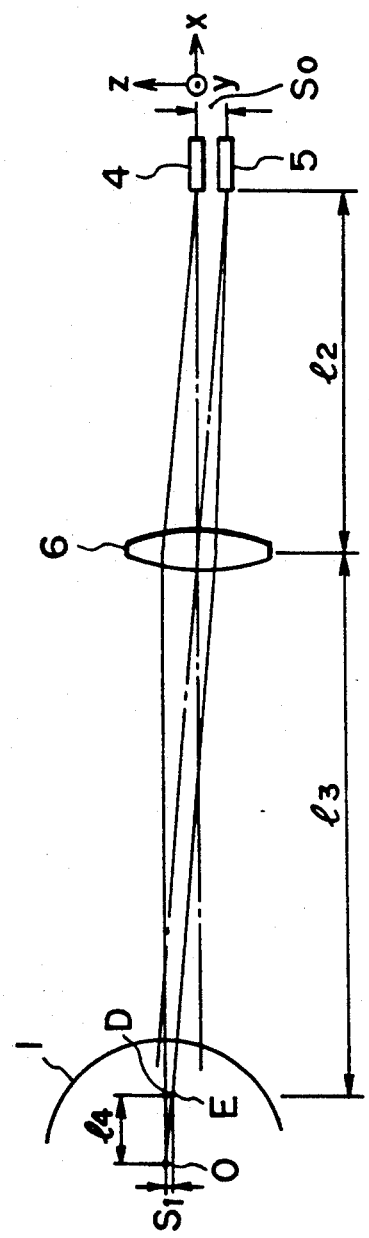
FIGS. 2A and 2B illustrate illumination means and optical means of FIG. 1.
Figure 2B:
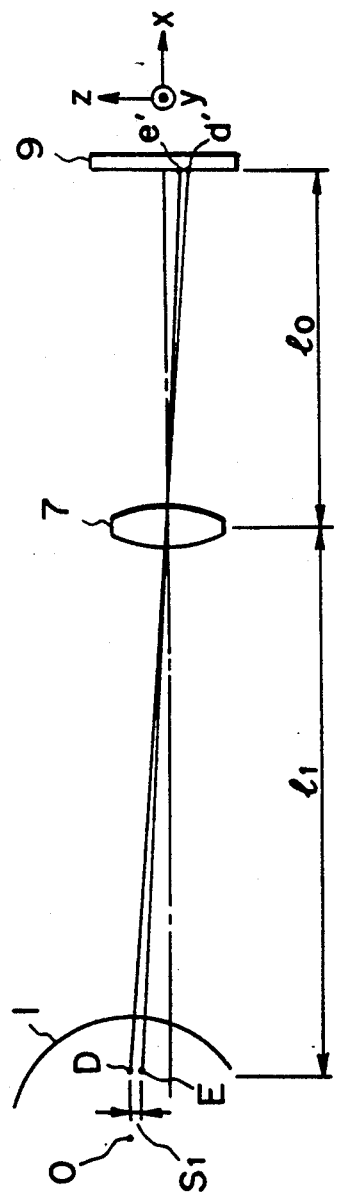

FIG. 1 shows a major part of a first embodiment of the present invention. FIGS. 2A and 2B illustrate illumination means and optical means of FIG. 1.

Numeral 101 denotes an eyeball of a subject (observer), numeral 1 denotes a cornea of the eyeball of the subject, numeral 2 denotes a sclera thereof, and numeral 3 denotes an iris thereof. Symbol O' denotes a center of rotation of the eyeball 101, O denotes a center of curvature of the cornea 1, a and b denote ends of the iris 3, and D and E denote positions at which first Purkinje's images appear due to light sources 4 and 5. Numerals 4 and 5 denote light sources such as light emitting diodes which emit infrared rays to which the object is insensitive. The light sources 4 and 5 are arranged in the vicinity of a focal plane of a projection lens 6 which substantially collimates the light beams from the light sources 4 and 5 to illuminate the plane of the cornea 1 through an half-mirror 10. The light source 4 is on the optical axis of the projection lens 6 and the light source 5 is arranged at a position which is displaced from the optical axis of the projection lens 6 by a distance $S_0$.

The light source 4 and the projection lens 6 form illumination means. Instead of providing the light sources 4 and 5 separately, two illuminated pinholes may be used.

Numeral 7 denotes a lens which focuses the first Purkinje's images D and E formed in the vicinity of the cornea 1 onto an image sensor 9 such as a CCD. The projection lens 6 and the lens 7 are co-axial by the half-mirror 10.

The lens 7 and the image sensor 9 form optical means. In the present embodiment, a linear image sensor is used because a visual axis on a horizontal line is detected, but a two-dimensional CCD is preferable when a vertical component is to be also detected. In this case, a scan signal at a desired position may be picked up.

Numeral 11 denotes calculation means which calculates the visual axis of the subject based on a working distance and the center position of the iris by making use of the output signal from the image sensor 9.

The optical source 5 and a portion of the calculation means 11 form distance detection means to be described later.

Symbol A denotes an optical axis of the lens 7 which coincides with an X-axis, and B denotes an optical axis of the eyeball which is inclined relative to the X-axis by an angle $\theta$.

Referring to FIGS. 2A and 2B, the features of the visual axis detector of the present embodiment and a method for detecting the distance from the eyeball of the subject to the predetermined plane (lens 7) of the detector are explained.

In FIGS. 2A and 2B, the half-mirror 10 is omitted.

The infrared rays emitted from the light sources 4 and 5 are collimated by the projection lens 6 to illuminate the cornea 1 of the eyeball. The first Purkinje's images D and E are generated by the light beams reflected by the surface of the cornea 1 at positions displaced from the center of curvature O of the cornea 1 by a distance $l_4 (\approx \gamma/2$, where $\gamma$ is a radius of curvature of the cornea 1). The point D is the first Purkinje's image for the light source 4 and has a coordinate $Z_D$, and the point E is the first Purkinje's image for the light source 5 and has a coordinate $Z_E$. Thus, $$S_1 = Z_D - Z_E \qquad (3)$$
$$\approx \frac{l_4}{l_2} \cdot S_0$$

where $l_2$ corresponds to a focal distance of the projection lens 6. The first Purkinje's images D and E are projected at coordinate positions d, and e, on the image sensor 9 by the lens 7 as shown in FIG. 2B. A distance $l_1$ between the lens 7 and the first Purkinje's image position (D or E) is represented by $$l_1 \approx \frac{S_1}{Z_{E'} - Z_{D'}} \cdot l_0 \qquad (4)$$
$$\approx \frac{S_0 \cdot l_0}{(Z_{E'} - Z_{D'})} \cdot \frac{l_4}{l_2}$$

where $l_1$ is a distance between the lens 7 and the first Purkinje's image, and $l_0$ is a distance between the lens 7 and the image sensor 9.

From the formula (4), the magnification $\beta$ of the optical system is represented by $$\beta = l_0/l_1 \qquad (5)$$
$$\approx \frac{Z_{E'} - Z_{D'}}{S_0} \cdot \frac{l_2}{l_4}$$

From the formulas (2) and (5), the rotation angle $\theta$ of the optical axis B of the eyeball is expressed by $$\sin\theta \approx \frac{Z_{a'} - Z_{b'} - 2Z_{D'}}{2(Z_{E'} - Z_{D'})} \cdot \frac{S_0}{l_2} \qquad (6)$$

where $Z_{a'}$ and $Z_{b'}$ are coordinates of the ends a and b of the iris 3 on the image sensor 9, and $\overline{OC} \approx l_4$ (where C is the mid-point between the ends a and b of the iris 3) in FIG. 1.

In the present embodiment, the formula (6) is calculated by the calculation means (11) to calculate the rotation angle $\theta$ of the optical axis B of the eyeball to determine the inclination of the visual axis of the eyeball so that the visual axis of the subject is detected. The signal relating to the iris image and the signal of the Purkinje's image can be fully discriminated because the intensity levels and the waveforms thereof are different from each other.

As described above, in the present embodiment, the distance detection light source 5 is provided in addition to the illumination light source 4 to precisely detect the visual axis of the subject. In the present embodiment, the iris illumination light source is shared by one of the Purkinje's image forming light sources, although the iris illumination light source may be separately provided.

Figure 3:
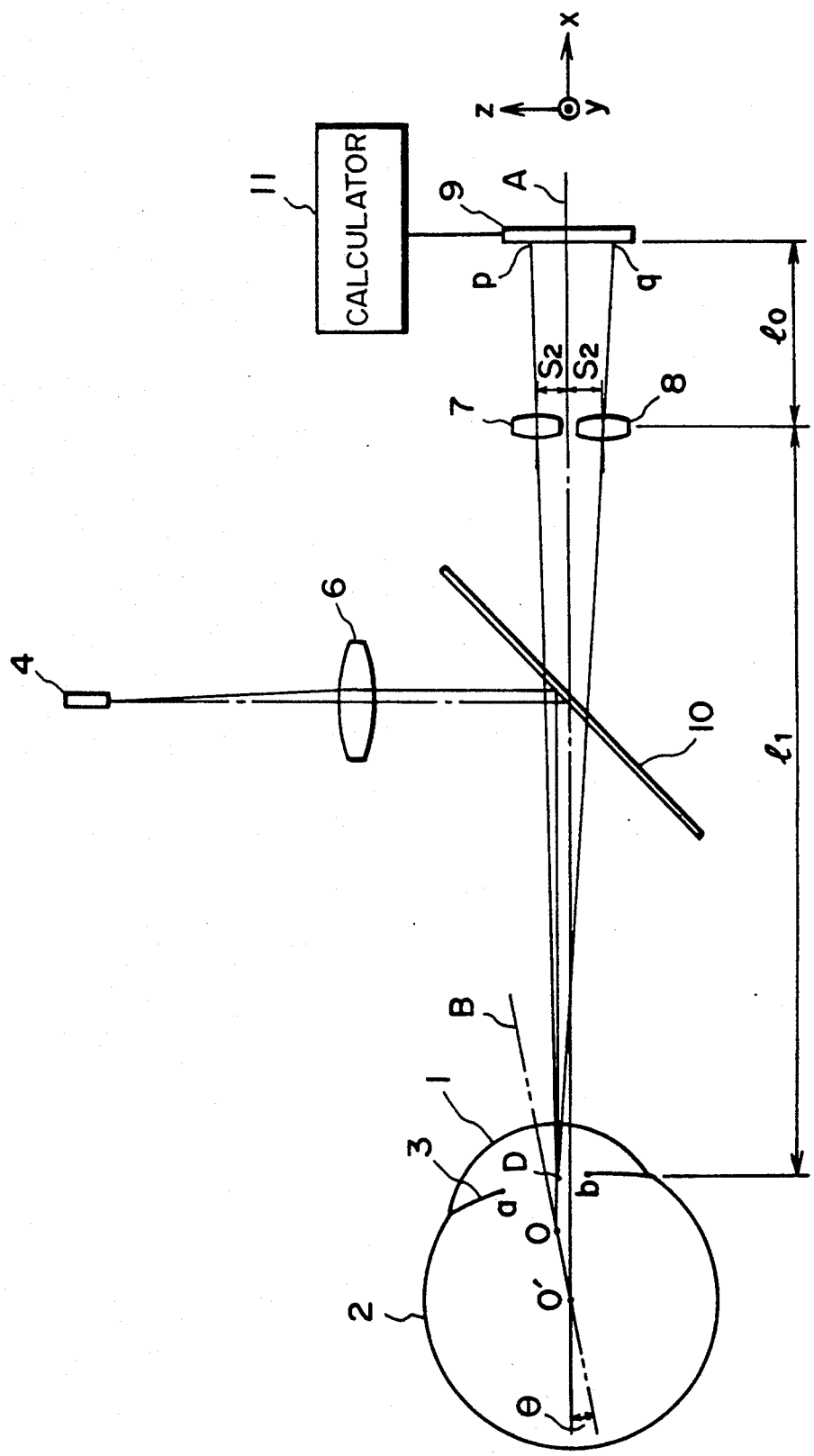
FIG. 3 shows an optical sectional view of a second embodiment of the present invention.

FIG. 3 shows a major part of a second embodiment of the present invention. The like elements to those shown in FIG. 1 are designated by like numerals.

Numeral 8 denotes a newly added lens whose optical axis is parallel to that of the lens 7.

In the present embodiment, a set of lenses 7 and 8 which function as the distance detection means are arranged to displace from an axis A (X axis) which relatively coincides with the optical axis of the projection lens 6 by a predetermined distance.

The infrared ray emitted from the light source 4 is collimated by the projection lens 6, reflected by the half-mirror 10 and illuminates the cornea 1. The first Purkinje's image D is formed by the infrared ray reflected by the surface of the cornea 1. The light beam from the first Purkinje's image D passes through the half-mirror 10 and is focused at positions P and Q on the image sensor 9 by the lenses 7 and 8.

The distance $l_1$ between the lens 7 or 8 and the first Purkinje's image position D is expressed by $$l_1 = \frac{S_2 + S_3}{Z_p - Z_q - (S_2 + S_3)} \cdot l_0 \quad (7)$$

where $Z_D$ is the Z coordinate of the first Purkinje's image position D, $Z_p$ is a Z coordinate of a projection position p on the image sensor 9 of the first Purkinje's image D by the lens 7, $Z_q$ is a Z coordinate of a projection position q on the image sensor 9 of the first Purkinje's image D by the lens 8, $S_2$ is a shift of the lens 7 from the X axis, $S_3$ is a shift of the lens 8 from the X axis, and $l_0$ is a distance between the lens 7 or 8 and the image sensor 9. From the formula (7), the magnification $\beta$ of the optical system is expressed by $$\beta = l_0/l_1 \quad (8)$$
$$= \frac{Z_p - Z_q - (S_2 + S_3)}{S_2 + S_3}$$

From the formulas (2) and (8), the rotation angle $\theta$ of the optical axis B of the eyeball is expressed by $$\sin\theta \approx \frac{(S_2 + S_3)(Z_a' - Z_b' - 2Z_p)}{\gamma\{Z_p - Z_q - (S_2 + S_3)\}} \quad (9)$$

where $Z_a'$ and $Z_b'$ are coordinates of projection images of the ends a and b of the iris 3 to the image sensor 9 by the lens 7.

In the present embodiment, the formula (9) is calculated by the calculation means 11 to detect the rotation angle $\theta$ of the optical axis B of the eyeball in order to determine the visual axis of the eyeball so that the visual axis of the subject is detected.

In this manner, in the present embodiment, the two lenses 7 and 8 are used, the first Purkinje's image are formed on the image sensor by the lenses 7 and 8, and the visual axis of the subject is accurately detected by making use of the coordinates of the first Purkinje's images formed on the image sensor and the distance $l_1$ from the first Purkinje's image to the lens 7 or 8.

As described above, in the present embodiment, the cornea is illuminated by the illumination means, the first Purkinje's images formed in the vicinity of the cornea are focused on the image plane by the optical means, and the visual axis of the subject is precisely detected by making use of the coordinates on the image plane and the distance information from the first Purkinje's image to the predetermined plane (for example, lens) of the optical means determined by the distance detection means, without needing the calibration of the visual axis by the subject himself.

Figure 4:
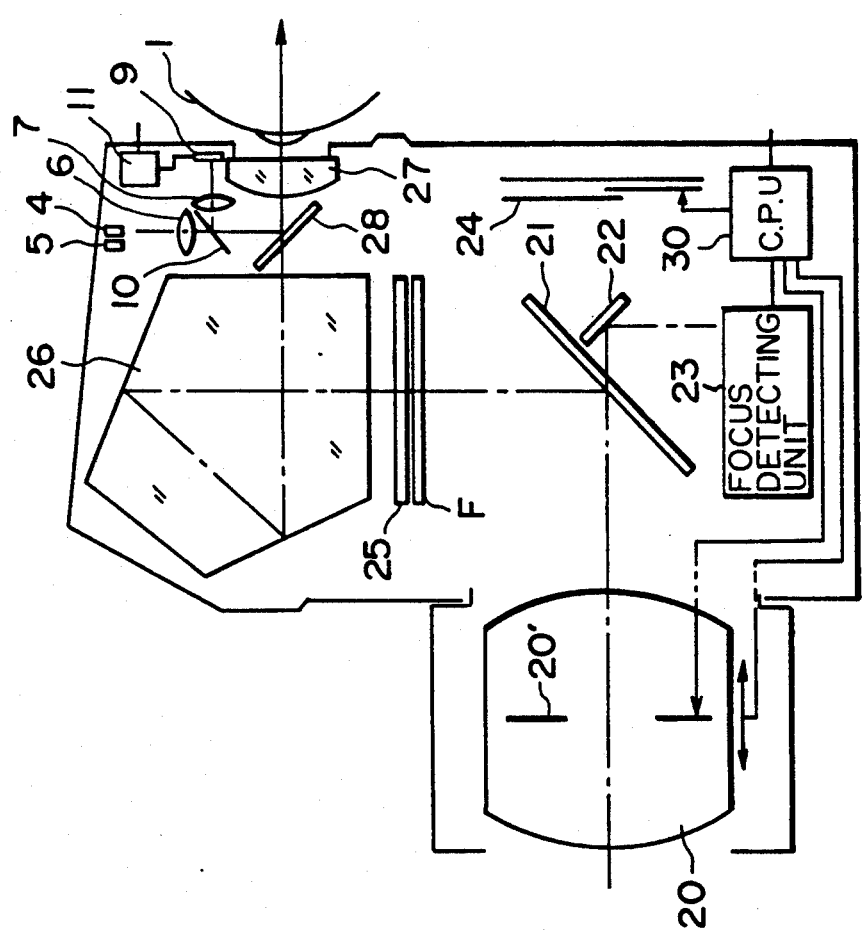
FIG. 4 shows an optical sectional view for illustrating incorporation of the device of FIG. 1 into a one-eye reflex camera.
Figure 6:
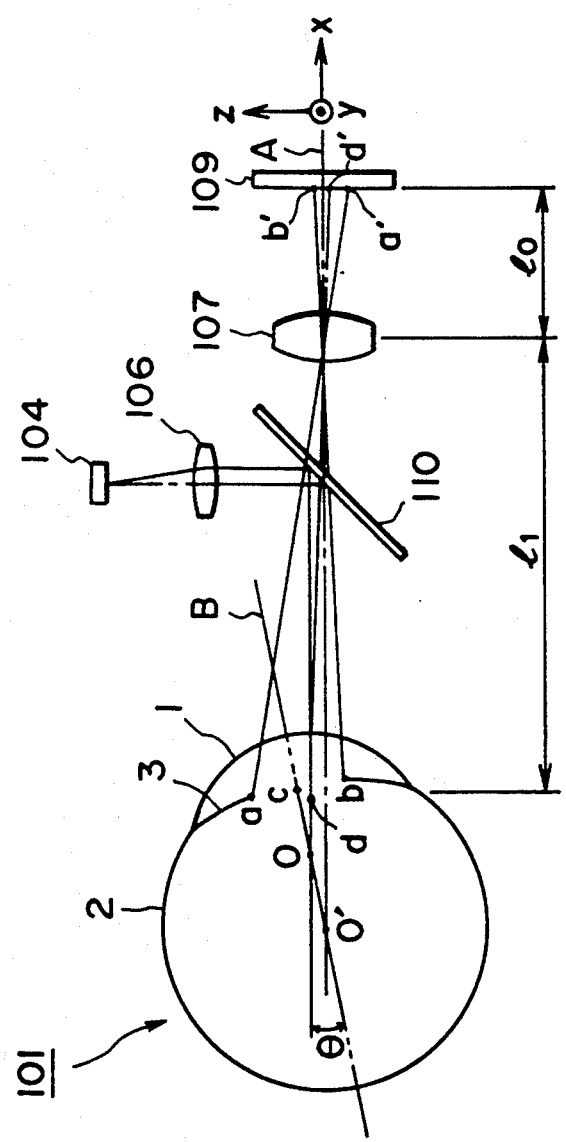
FIG. 6 shows, in a modified form, a prior art visual axis detector.

The arrangement when a visual axis detector carrying out the above-described method is incorporated into a camera body is shown in FIG. 4.

Figure 5:
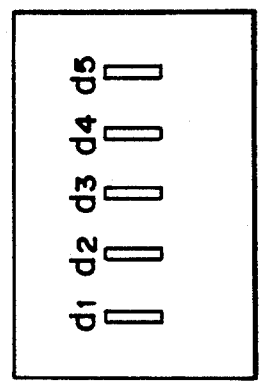
FIG. 5 shows an information display plate which displays distance measuring field marks.

In FIG. 4, the reference numeral 20 designates a fixed or removably mounted photo-taking lens which is focus-adjusted by a driver, not shown. The reference numeral 20' denotes an aperture diaphragm. The reference numeral 21 designates a main mirror which reflects most of the light beam passed through the photo-taking lens 20 and transmits a part of such light beam therethrough. The reference numeral 22 denotes a sub-mirror which reflects the light beam transmitted through the main mirror 21 toward the bottom portion of the camera body. The reference numeral 23 designates a well-known focus detecting unit having a plurality of distance measuring fields. The reference numeral 24 denotes a shutter, the letter F designates a focusing screen used when detection is effected visually, and the reference numeral 25 denotes an information display plate which displays distance measuring field marks d1–d5, for example, in the photographing screen as shown in FIG. 5, the reference numeral 26 designates a pentagonal roof prism and the reference numeral 27 denotes an eyepiece. The reference numeral 28 designates an optical path dividing mirror which may be, for example, a dichroic mirror which transmits the visible light therethrough and reflects the infrared light.

The microprocessor 30 controls the operations of the aperture 20' and the shutter 24 in conformity with selected photographing mode.

As explained in connection with FIG. 1, the microprocessor 30 detects which position of d1–d5 in FIG. 5 the photographer is attempting to focus upon, based on the signal produced by the calculation means 11. Then, the microprocessor 30 calculates a focusing error based on a signal from a detector (not shown) which is at a selected position of the focus detecting unit 23, and adjusts the focus of the photo-taking lens 20 to compensate for the focusing error.

We claim:

1. An optical apparatus, comprising:
   an observation means with which an observer observes an object;
   an image sensor for generating a signal in response to an image;
   optical means for forming a plurality of reflected light source images on said image sensor by the reflection of a common surface of a front eye part of an observer;

said optical means having (1) an illumination assembly for projecting a light beam from at least one light source to the eye of the observer, and (2) a convergence component having at least one convergent lens for converging the light beam reflected from the eye of the observer, one of (1) said at least one light source and (2) said at least one convergent lens comprising a plurality, to produce the plurality of reflected light source images; and means electrically coupled to said image sensor for generating (1) information relating to a relative position between the plurality of reflected light source images reflected from the eye, and (2) information relating to the reflected image of a front eye part, to generate information relating to a direction of the visual axis of the eye.

2. An optical apparatus according to claim 1 wherein said illumination assembly includes a plurality of light sources and a projection lens for projecting the light beams from said light sources, and wherein said convergence component comprises a lens coaxial to said projection lens.

3. An optical apparatus according to claim 2 wherein the light beam passed through said projection lens is substantially colliminated.

4. An optical apparatus according to claim 1 wherein said illumination assembly includes a light source and a projection lens for projecting a light beam from the light source, and wherein two convergent lenses are provided.

5. An optical apparatus according to claim 4 wherein the light beam passed through said projection lens is substantially colliminated.

6. An optical apparatus according to claim 1 wherein said common surface is a cornea and said reflected image of a front eye part is an iris image.

7. An optical apparatus according to claim 1 wherein said information relating to the front eye part reflected image is information relating to a position corresponding to a center of the iris on the image sensor.

8. A photographing device comprising:
imaging means for receiving an object image from a photo-taking lens;
a viewer through which the object image is observed by an observer;
visual axis detection means including an image sensor for generating a signal in response to an image, forming means for forming a plurality of reflected light source images on said image sensor by the reflection from a cornea of the observer, said forming means having a projection part for projecting a light beam to an eye of an observer and an optical part for receiving the light from the eye of the observer, and signal processing means for forming visual axis information relating to the visual axis by calibrating with information relating to a working distance between said visual axis detection means and the observer when said signal is processed; and
control means for generating a signal to control the photographing device in accordance with the visual axis information.

9. A photographing device according to claim 8 wherein said projection part has a plurality of light sources and a projection lens for projecting light beams from the light sources, and wherein said optical part has a lens coaxial to said projection lens.

10. A photographing device according to claim 8 wherein said projection part has a light source and a projection lens for projecting the light beam from the light source, and wherein said optical part has a plurality of lenses.

11. An optical apparatus, comprising:
an observation means with which an observer observes an object;
an image sensor for generating a signal in response to receiving an image;
optical means for forming on said image sensor a plurality of reflected light source reflected from an eye of the observer;
said optical means having (1) an illumination assembly for projecting light beams from two light sources to the eye of the observer, and (2) a convergence component having one convergent lens for converging the light beams reflected from the eye of the observer to produce the plurality of reflected light source images; and
means electrically coupled to said image sensor for generating (1) information relating to a relative position between the plurality of reflected light source images, and (2) information relating to the reflected image of an eye, to generate information relating to a direction of the visual axis of the eye.

12. An optical apparatus according to claim 11, wherein said convergence component comprises two convergent lenses.

13. An optical apparatus according to claim 11 wherein said illumination assembly includes a projection lens for projecting the light beams from said light sources, and said convergence component is coaxial with said projection lens.

14. An optical apparatus according to claim 13 wherein the light beam passed through said projection lens is substantially colliminated.

15. An optical apparatus according to claim 11 wherein said plurality of reflected light source images arise from reflections of the cornea and iris.

16. An optical apparatus, comprising:
an observation means with which an observer observes an object;
an image sensor for generating a signal in response to receiving an image;
optical means for forming on said image sensor a plurality of reflected light source images reflected from an eye of the observer;
said optical means having (1) an illumination assembly for projecting a light beam from a light source to the eye of the observer, and (2) a convergence component having two convergent lenses for converging the light beam reflected from the eye of the observer to produce the plurality of reflected light source images; and
means electrically coupled to said image sensor for generating (1) information relating to a relative position between the plurality of reflected light source images, and (2) information relating to the reflected image of an eye, to generate information relating to a direction of the visual axis of the eye.

17. An optical apparatus according to claim 16 wherein said illumination assembly comprises two light sources.

18. An optical apparatus according to claim 16 wherein said illumination assembly includes a projection lens for projecting the light beams from said light sources.

19. An optical apparatus according to claim 18 wherein the light beam passed through said projection lens is substantially collimated.

20. An optical apparatus according to claim 16 wherein said plurality of reflected light source images arise from reflections of the cornea and iris.

21. A photographic camera, comprising:
a viewer through which an object image is observed;
visual axis detection means including an image sensor for generating a signal in response to reception of the image;
forming means for converging light reflected from the eye of an observer onto said image sensor, said forming means having a projection part for projecting a light beam to the eye and an optical part for receiving the light beam reflected from the eye;
signal processing means for calculating information converging a working distance between the eye and said viewer on the basis of an output of said image sensor, and for forming visual axis information relating to the eye visual axis by calibrating the information relating to the working distance; and
control means for generating a signal to control a focus detection device in accordance with the visual axis information.

22. A camera according to claim 21, wherein said focus detection device includes a plurality of detection areas within the field of view of said viewer.

23. A camera according to claim 21, wherein said projection part has a plurality of light sources and a projection lens for projecting light beams from the light sources, and wherein said optical part has a lens coaxial with said projection lens.

24. A camera according to claim 21, wherein said projection part has a light source and a projection lens for projecting the light beam from the light source, and wherein said optical part has a plurality of lenses.

* * * * *

UNITED STATES PATENT AND TRADEMARK OFFICE
CERTIFICATE OF CORRECTION

PATENT NO. : 5,225,862
DATED : July 6, 1993
INVENTOR(S) : AKIHIKO NAGANO, ET AL.

It is certified that error appears in the above-indentified patent and that said Letters Patent is hereby corrected as shown below:

ON THE COVER PAGE

[54] TITLE

"IMAGE" should read --IMAGES--.

COLUMN 1

Line 3, "IMAGE" should read --IMAGES--.
Line 64, "curvature 0" should read --curvature O--.

COLUMN 2

Formula 2, "$\frac{Za'+Zb'}{2} - Zd'$" should read --$\frac{Za'-Zb'}{2} - Zd'$--.

Line 44, "to" should be deleted.
Line 67, "source" should read --sources--.

UNITED STATES PATENT AND TRADEMARK OFFICE
CERTIFICATE OF CORRECTION

PATENT NO. : 5,225,862

DATED : July 6, 1993

INVENTOR(S) : AKIHIKO NAGANO, ET AL.

It is certified that error appears in the above-indentified patent and that said Letters Patent is hereby corrected as shown below:

COLUMN 4

Line 22, "coordinate ZD," should read --coordinate $Z_D$,--.
Line 24, "ccordinate ZE." should read --coordinate $Z_E$.--.

COLUMN 6

Line 2, "are" should read --is--.

COLUMN 9

Line 18, "converging" should read --concerning--.

Signed and Sealed this

Twenty-ninth Day of March, 1994

Attest:

BRUCE LEHMAN

*Attesting Officer*   *Commissioner of Patents and Trademarks*